United States Patent
Hwang et al.

(10) Patent No.: US 6,387,333 B2
(45) Date of Patent: May 14, 2002

(54) GAS PURIFYING SYSTEM

(75) Inventors: Jung-Sung Hwang; Tae-Ho Kim; Soon-Young Lee; Jae-Heung Choi, all of Yongin (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/816,367

(22) Filed: Mar. 26, 2001

(30) Foreign Application Priority Data

Jun. 20, 2000 (KR) .............................. 00-33832

(51) Int. Cl.[7] .............................................. A62B 11/00
(52) U.S. Cl. .................. 422/121; 422/243; 422/186.04; 422/186.01; 55/223; 55/233
(58) Field of Search ................ 422/121, 243; 55/223

(56) References Cited

U.S. PATENT DOCUMENTS 4,806,148 A * 2/1989 Ottengraf ..................... 55/223
5,380,503 A * 1/1995 Fujii et al. .................. 422/243

FOREIGN PATENT DOCUMENTS

| JP | 4-239131 | 8/1992 |
| JP | 6-252242 | 9/1994 |

* cited by examiner

*Primary Examiner*—Robert J. Warden, Sr.
*Assistant Examiner*—Sean E. Conley
(74) *Attorney, Agent, or Firm*—Volentine Francos, PLLC

(57) ABSTRACT

A gas purifying system includes a water spraying system, and a collecting apparatus installed downstream of the water spraying system. The collecting apparatus has a surface composed of an electron emitting material, and the electron emitting material is capable of emitting electrons when subjected to visible light, ultraviolet light or electrical energy. The system can also include an ultraviolet lamp, with an ultraviolet photoelectron emitting material surrounding the ultraviolet lamp. The ultraviolet lamp and the ultraviolet photoelectron emitting material are positioned between the water spraying system and the collecting apparatus.

13 Claims, 9 Drawing Sheets

GAS PURIFYING SYSTEM

BACKGROUND OF THE INVENTION

1. Field of the Invention

The present invention relates to a gas purifying system, and more particularly, to a gas purifying system for effectively eliminating contaminating materials emanating from production equipment, equipment operators, and the ambient production environment in general.

2. Description of the Related Art

Particulate contamination during the semiconductor device manufacturing process greatly increases the likelihood of device failure. In particular, a highly purified gaseous atmosphere is required to control fine particles (i.e., atomic or molecular sized gaseous contaminating particles) on or near the surface of a semiconductor substrate. The sources of these contaminating particles are numerous, including the production equipment, the equipment operators, the ambient production environment, and the process gases, acids and bases, organic contaminants, etc., used in manufacturing a semiconductor device.

Purification systems are thus very important for the productivity and proper operation of a semiconductor device, and many methods are employed to control or eliminate contaminating particles.

For example, semiconductor devices are manufactured and managed in a clean room. In the clean room, various filters, water showering systems (WSS), etc. are employed to collect and remove the contaminating materials. Generally, about 400–600 filters are installed in a single clean room.

Filters employed in the clean room are typically active carbon filters or ion exchange filters (IEF). The active carbon filter is manufactured by pulverizing active carbon, compression molding the pulverized active carbon, and then coating a material thereon which attracts or collects a specific contaminating component. The active carbon filter is utilized for removing ozone, organic materials, SOx, NOx, etc. The IEF filter is manufactured by combining fiber with various chemical functional groups and is utilized for collecting ions such as ammonium cation.

The WSS produces minute water droplets formed by spraying water through nozzles. Floating dust within an air stream collides with these water droplets and become adsorbed, and then they are eventually removed.

Figure 1A:
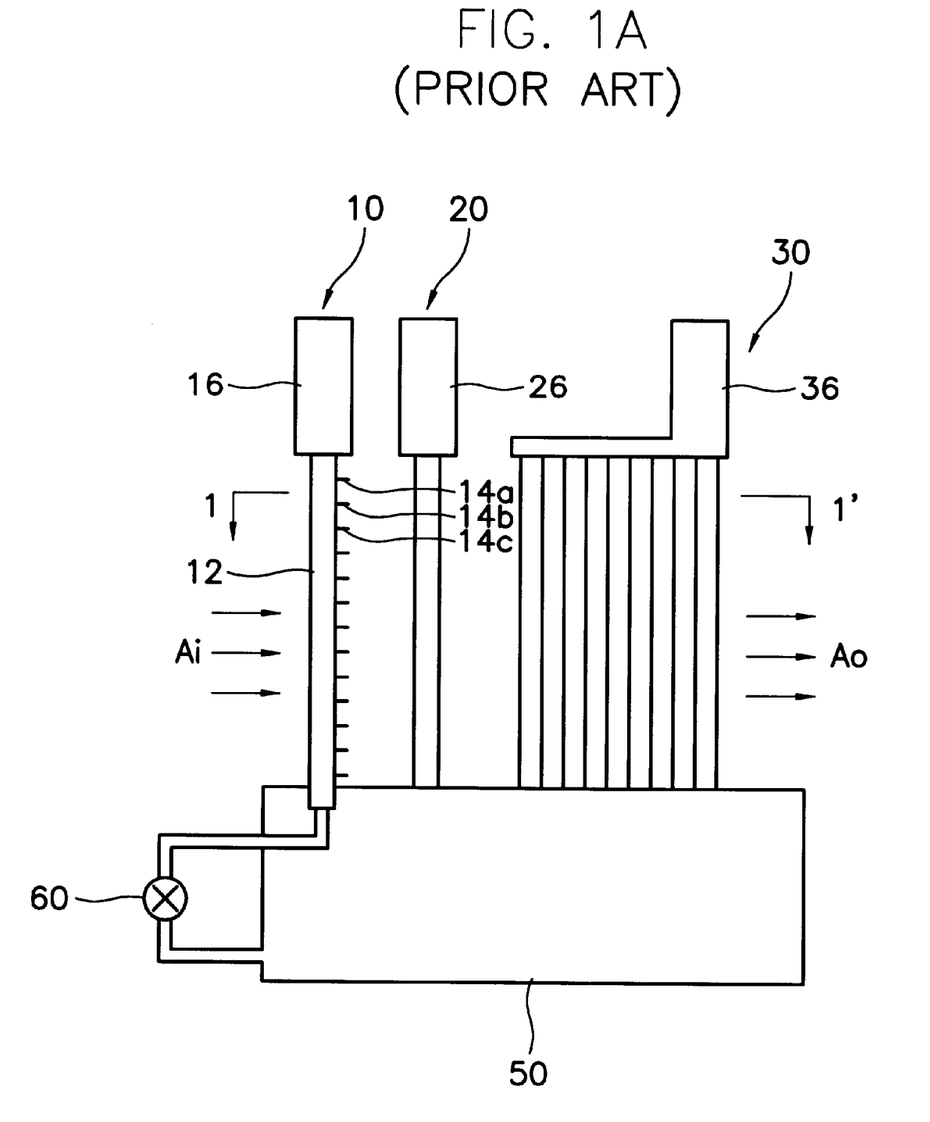
Figure 1B:
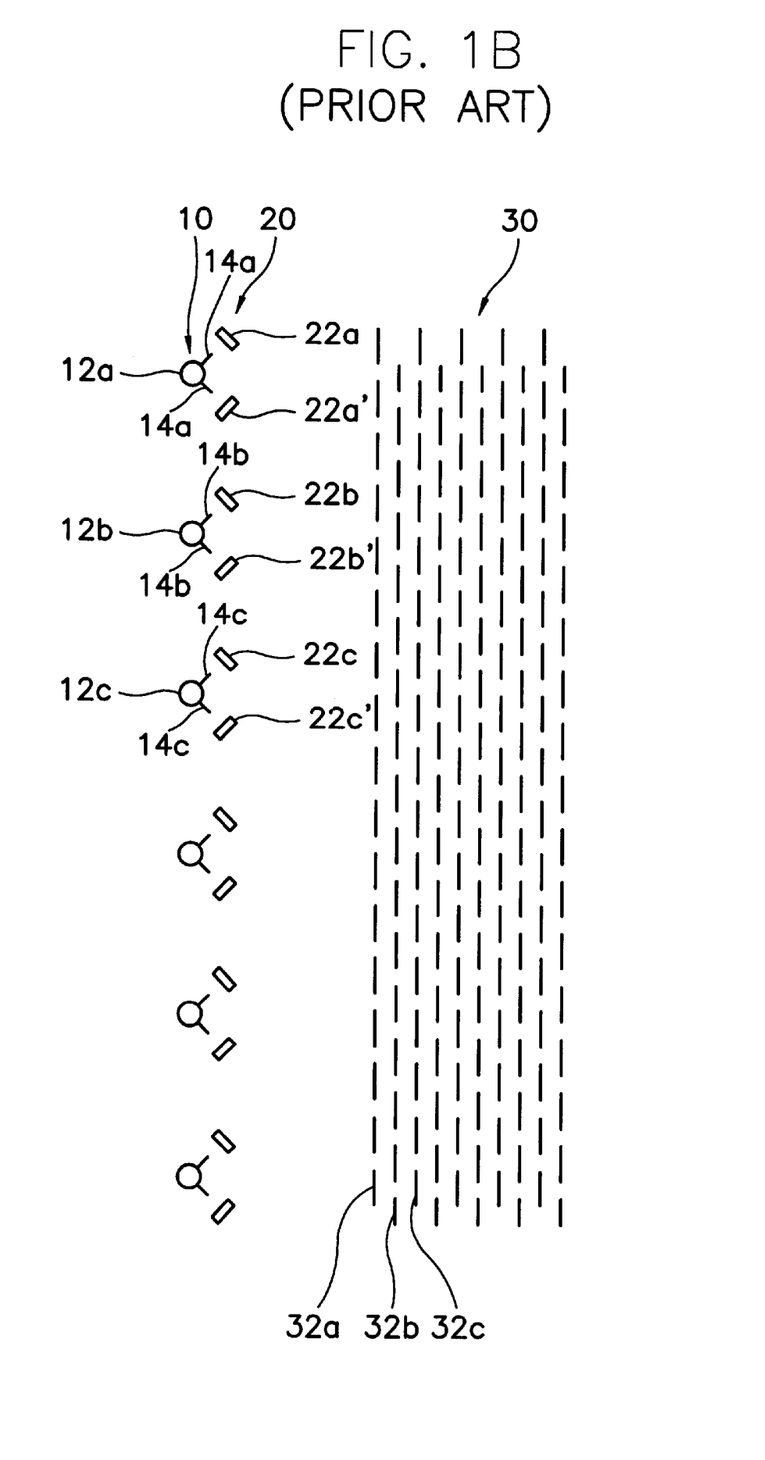

FIGS. 1A and 1B are schematic diagrams of a conventional WSS in which FIG. 1A is a side view and FIG. 1B is a partial top view taken along a line 1–1' in FIG. 1A. The conventional WSS includes the following: a water spraying system 10 having a plurality of nozzles 14a, 14b, 14c, etc., for producing minute water droplets; a crash plate 20 for separating the water droplets into minute droplets having a smaller size than the water droplets; an eliminator 30 with which the water droplets collide and then fall downward; and a tank 50 for collecting the falling water droplets and storing this collected water until the collected water is provided to the water spraying system 10. In operation, potentially contaminated in-flowing air Ai is introduced into the WSS through the water spraying system 10, it passes through the crash plate 20 and the eliminator 30 along a path designated by the arrows, and it is then exhausted out as clean out-flowing air Ao.

The water spraying system 10 is provided with a plurality of vertically extending water transferring pipes 12a, 12b, 12c, . . . 12n, and a plurality of nozzles 14a, 14b, 14c, . . . 14n, configured in at least one vertical line on each of the water transferring pipes. A water transferring pipe supporter 16 supports the water transferring pipes 12a, 12b, 12c, . . . 12n.

Water supplied from the tank 50 by means of a pump 60 moves upward along the water transferring pipes 12a, 12b, 12c, . . . 12n, and then is rapidly sprayed through the nozzles 14a, 14b, 14c, . . . 14n. In this embodiment the nozzles are arranged in two vertical columns on the water transferring pipes, preferably with a predetermined angle larger than 90° separating the columns. The size of the sprayed water droplets can be controlled, and is determined by the size of the nozzles 14a, 14b, 14c . . . 14n, and the water pressure. Preferred droplet size is about 100 μm or less for optimal effect in removing the contaminating material.

The water droplets sprayed from the nozzles 14a, 14b, 14c . . . 14n, impact the crash plate 20, which comprises a plurality of vertically extending long plates 22a, 22a', 22b, 22b', . . . 22n, 22n' so that the water droplets are divided into smaller droplets. When the size of the water droplets becomes smaller, the overall effective surface area of the group of droplets becomes larger. Thus, the adsorbing effect of the droplets for the contaminating material increases. For each of the water transferring pipes (e.g., 12a), two corresponding plates (e.g., 22a, 22a') are installed. The plates 22a, 22a', 22b, 22b', . . . 22n, 22n' are supported by a crash plate supporter 26 and are provided perpendicular to the direction of the sprayed water from the nozzles (e.g., 14a) as shown in FIG. 1B.

Water droplets, which have passed through the crash plate 20, collide with the eliminator 30. The eliminator 30 is manufactured from a plastic material or SUS (stainless steel) and preferably has a porous plate shape. The eliminator 30 comprises a plurality of eliminating plates 32a, 32b, 32c, . . . 32n, as shown in FIG. 1B. The eliminating plates 32a, 32b, 32c, . . . 32n, are installed so that the openings through the adjacent eliminating plates are offset, and are supported by an eliminator supporter 36. In such an arrangement, water droplets containing contaminating material passing through a front eliminating plate 32a might collide with a rear eliminating plate 32b or 32c.

Since it is positioned under the water spraying system 10, the crash plate, 20 and the eliminator 30, the tank 50 collects the water droplets containing the contaminating materials, which have collided with the crash plate 20 and the eliminator 30. The collected water is stored in the tank 50 until the water is provided to the water spraying system 10 again. The recirculation time is determined by periodically measuring the electrical resistance of the water in the tank 50. When the water contains a large amount of contaminating material, the resistance thereof increases. Generally, a predetermined amount of water is injected while the same amount of water is exhausted out to keep the resistance of the water at a constant value.

By utilizing the above described filtering and WSS gas purifying systems, various contaminating components including floating dust and aqueous contaminating materials can be advantageously removed.

However, non-aqueous contaminating materials and organic contaminating materials cannot be satisfactorily removed. In particular, when a large amount of gas passes rapidly, the contaminating material contained in the gas also passes rapidly, which minimizes the amount of time the contaminating material can impact the water droplets. In addition, for sub-micron particles, the removing efficiency of the non-aqueous and organic gas contaminating materials and minute particles is poor.

Indeed, among the causes for deterioration in production yields of semiconductor devices, it is believed that 80% or more are caused by minute particle contamination. As the integration density of semiconductor devices increases, tighter controls on gaseous contaminating materials is required. Furthermore, since the lifetime of the above-described filters and WSS is limited, replacement of the filters, and the maintenance/upkeep of the nozzles and eliminator are required.

Research is being conducted on gas purifying systems utilizing ultraviolet light. According to this principle, photoelectrons generated by an ultraviolet ray attach themselves to the minute particles in the air, and this combination is then collected by an electrode. Japanese Laid-Open Patent No. Hei 6-252242 discloses a gas purifying system including a photoelectron emitting material, ultraviolet source and/or an exposing light source, and an electrode in a closed space. In this system, the particles in the air are charged by the photoelectrons generated by the ultraviolet light and then collected by the electrode.

Japanese Laid-Open Patent No. Hei 4-239131 discloses a method of charging minute particles on the surface and near the wafer by exposing the minute particles to an ultraviolet ray and collecting the charged particles to remove them. U.S. Pat. No. 5,380,503 discloses a method of purifying gas in an isolated space. In this patent, an electric field is formed between an electrode and a photoelectron emitting material. Particles in the space attach to the photoelectron generated from the photoelectron emitting material by an ultraviolet lamp, and are then collected by an electrode.

However, since the above-described methods are applied in the isolated space, the instruments are small. Accordingly, these systems are mostly used for cleaning a small limited space in which high purity is very important, such as a space used for storing goods.

SUMMARY OF THE INVENTION

In view of the above, it is an object of the present invention to provide a gas purifying system by which molecular contaminating materials, including non-aqueous and organic contaminating materials as well as aqueous contaminating materials, can be advantageously removed.

To achieve this and other objects, the present invention provides a gas purifying system including a water spraying system. A collecting apparatus is installed at the rear portion (downstream) of the water spraying system. The surface of the collecting apparatus is manufactured from a material that can emit electrons when subjected to visible light, ultraviolet light, or electrical energy.

According to the present invention, aqueous contaminating materials and floating dust can be initially removed by the minute water droplets in the water spraying system, and then organic and non-aqueous contaminating materials can be secondarily removed by an interaction of the water droplets with the electrons.

BRIEF DESCRIPTION OF THE DRAWINGS

The above object and advantages of the present invention will become more apparent by describing preferred embodiments in detail with reference to the attached drawings in which:

FIGS. 1A and 1B are schematic diagrams of a conventional WSS in which FIG. 1A is a side view and FIG. 1B is a partial top view taken along a line 1–1' in FIG. 1A;

FIGS. 2A through 2C are schematic views of a gas purifying system according to a first embodiment of the present invention, in which FIG. 2A is a side view, FIG. 2B is a partial top view taken along a line 2–2' in FIG. 2A, and FIG. 2C is a partial enlarged front view of a collector;

FIGS. 5A and 5B are schematic views of a gas purifying system according to a third embodiment of the present invention of the present invention, in which FIG. 5A is a side view and FIG. 5B is a partial enlarged view of FIG. 5A.

DESCRIPTION OF THE PREFERRED EMBODIMENT

Figure 2A:
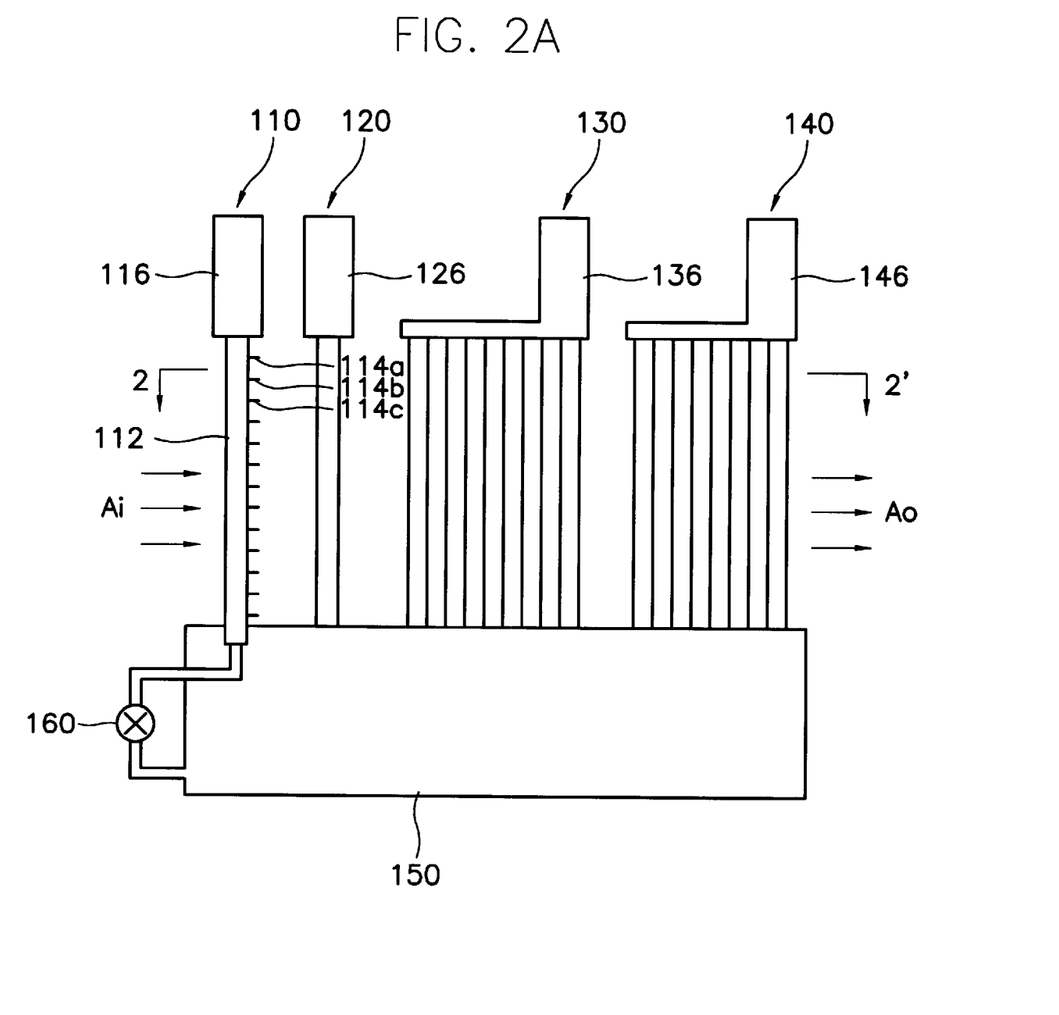
Figure 2B:
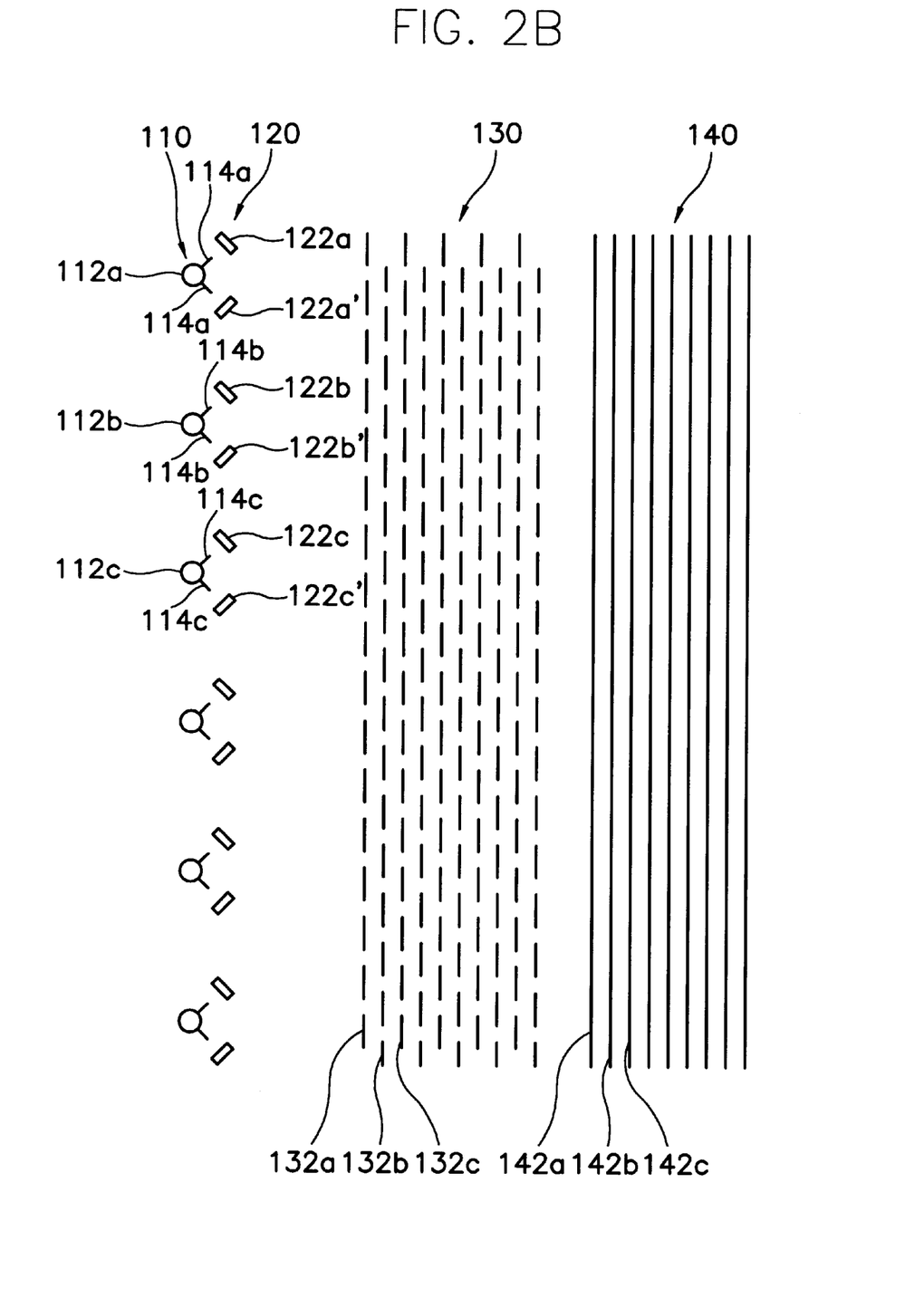
Figure 2C:
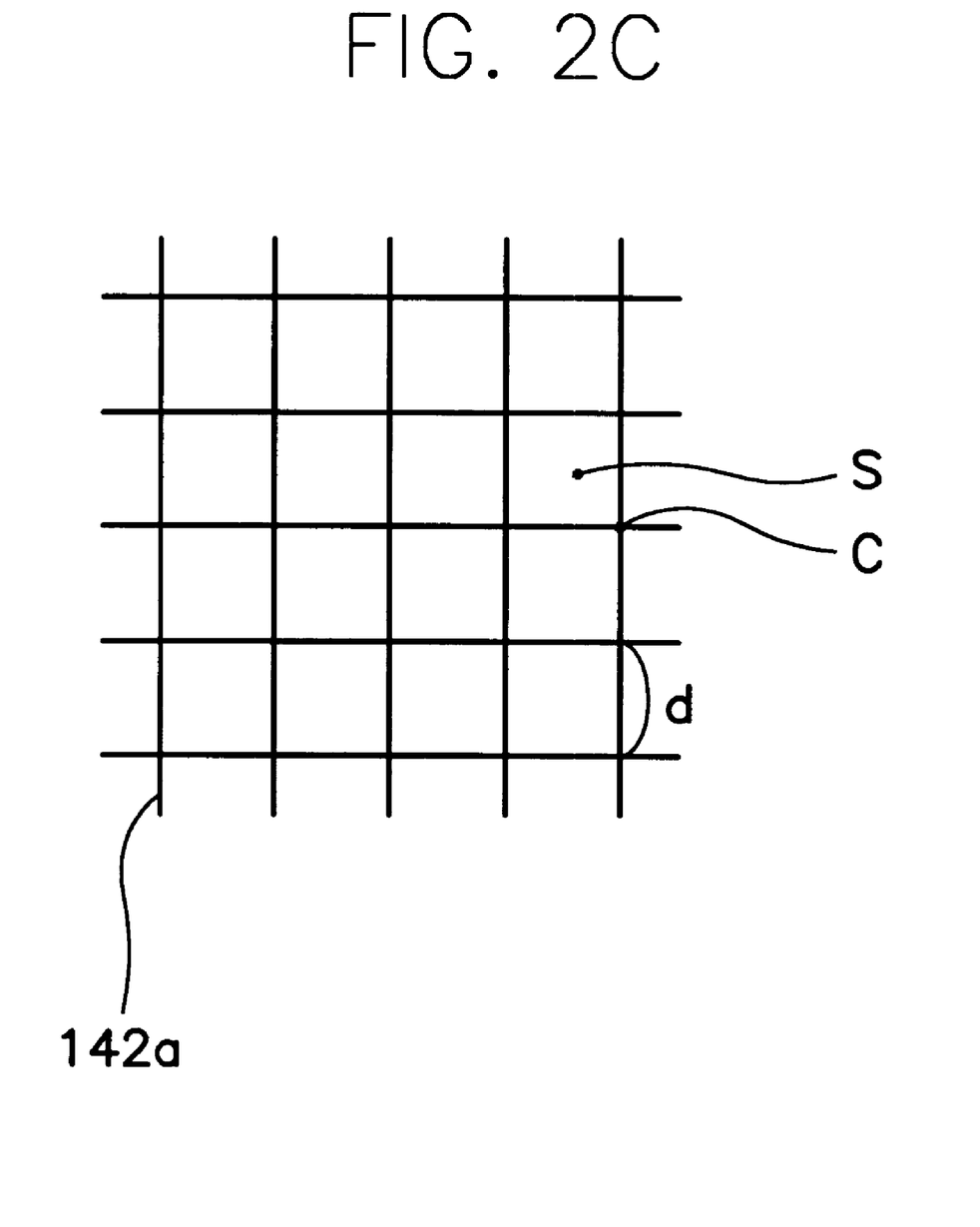

FIGS. 2A through 2C are schematic views of a gas purifying system according to a first embodiment of the present invention. FIG. 2A is a side view of the embodiment, FIG. 2B is a partial top view taken along a line 2–2' in FIG. 2A, and FIG. 2C corresponds to a partial enlarged front view of a collector.

In its broadest sense, the gas purifying system of the present invention includes a conventional WSS, similar to that illustrated in FIGS. 1A and 1B, positioned in the front portion, and a collecting apparatus which is provided at the rear portion (downstream) of the WSS, and which can emit electrons when subjected to visible light, ultraviolet light or electrical energy.

More specifically, the gas purifying system according to this embodiment includes a water spraying system 110 having a plurality of nozzles 114a, 114b, 114c, etc., for producing minute water droplets; a crash plate 120 for separating the water droplets into minute droplets smaller than the water droplets; an eliminator 130 with which the water droplets collide and then fall downward; and a tank 150 for collecting the falling water droplets and storing this collected water until the collected water is provided to the water spraying system 110. In operation, potentially contaminated inflowing air Ai is introduced into the WSS through the water spraying system 110, it passes through the crash plate 120 and the eliminator 130 along a path designated by the arrows, and it is then exhausted out as clean out-flowing air Ao.

The water spraying system 110 is provided with a plurality of vertically extending water transferring pipes 112a, 112b, 112c, ... 112n, and a plurality of nozzles 114a, 114b, 114c, ... 114n, configured in at least one vertical line on each of the water transferring pipes. A water transferring pipe supporter 116 supports the water transferring pipes 112a, 112b, 112c, ... 112n.

Water supplied from the tank 150 by means of a pump 160 moves upward along the water transferring pipes 112a, 112b, 112c, ... 112n and then is rapidly sprayed through the nozzles 114a, 114b, 114c, ... 114n. In this embodiment the nozzles are arranged in two vertical columns on the water transferring pipes, preferably with a predetermined angle larger than 90° separating the columns. The size of the sprayed water droplets can be controlled, and is determined by the size of the nozzles 114a, 114b, 114c, ... 114n, and the water pressure. Preferred droplet size is about 100 $\mu$m or less for optimal effect in removing the contaminating material.

The water droplets sprayed from the nozzles 114a, 114b, 114c, ... 114n impact the crash plate 120, which comprises a plurality of vertically extending long plates 122a, 122a', 122b, 122b', ... 122n, 122n' so that the water droplets are divided into smaller droplets. When the size of the water droplets becomes smaller, the overall effective surface area of the group of droplets becomes larger. Thus, the adsorbing effect of the droplets for the contaminating material increases. For each of the water transferring pipes (e.g., 112a), two corresponding plates (e.g., 122a, 122a') are installed. The plates 122a, 122a', 122b, 122b', 122n, 122n' are supported by a crash plate supporter 126 and are provided perpendicular to the direction of the sprayed water from the nozzles (e.g., 114a) as shown in FIG. 2B.

Water droplets, which have passed through the crash plate 120, collide with the eliminator 130. The eliminator 130 is manufactured from a plastic material or SUS (stainless steel) and preferably has a porous plate shape. The eliminator 130 comprises a plurality of eliminating plates 132a, 132b, 132c, ... 132n as shown in FIG. 2B. The eliminating plates 132a, 132b, 132c, ... 132n are installed so that the openings through the adjacent eliminating plates are offset, and are supported by an eliminator supporter 136. In such an arrangement, water droplets containing contaminating material passing through a front eliminating plate 132a might collide with a rear eliminating plate 132b or 132c.

Since it is positioned under the water spraying system 110, the tank 150 collects the water droplets containing the contaminating materials, which have collided with the crash plate 120 and the eliminator 130. The collected water is stored in the tank 150 until the water is provided to the water spraying system 110 again. The recirculation time is determined by periodically measuring the electric resistance of the water in the tank 150. When the water contains a large amount of contaminating material, the resistance thereof increases. Generally, a predetermined amount of water is injected while the same amount of water is exhausted out to keep the resistance of the water at a constant value.

The collecting apparatus 140 is installed at the rear portion and downstream of the eliminator 130. The collecting apparatus is manufactured by integrating and arranging with a predetermined interval a plurality of collecting plates 142a, 142b, 142c, ... 142n, that are formed from, or coated by, a component such as ZnO, CdS, $WO_3$, $TiO_2$, etc., which have the characteristic that they can emit electrons by exposure to visible light, ultraviolet light, or electrical energy.

The shape of the collecting plates 142a, 142b, 142c, ... 142n may take various forms. For example, they may be a porous plate in which a plurality of holes are formed therein, a mesh-shaped plate which is manufactured by crossing wires at approximately 90 degree angles, or a honey comb-shaped plate which is manufactured by bending wires into a hexagon shape. FIG. 2C illustrates an exemplary mesh-shaped plate 142a.

For the mesh-shaped plates 142a, 142b, 142c, ... 142n, the collecting efficiency of the contaminating materials is determined by a distance 'd' between the meshes, and the number of adjacent mesh-shaped collecting plates employed. When arranging the adjacent collecting plates, it is preferable that they are offset from each other. This offset is depicted in FIG. 2C, wherein the mesh intersection point 'c' of a front plate is oriented to confront a space 's' of a rear collecting plate. This ensures that a large amount of air will collide with the collecting plates.

As the distance 'd' becomes smaller, the collecting efficiency of the contaminating materials increases. However, if the distance 'd' is too small, the flow of the air begins to become obstructed, which increases the manufacturing cost. Therefore, an appropriate distance 'd' can be determined considering these factors, and without undue experimentation.

Furthermore, as the number of collecting plates 142a, 142b, 142c, ... 142n, increases, the collecting efficiency of the contaminating material also increases. However, one must consider the amount of space for installing the collecting plates, and the cost, when determining the appropriate number of collecting plates to employ.

Figure 3A:
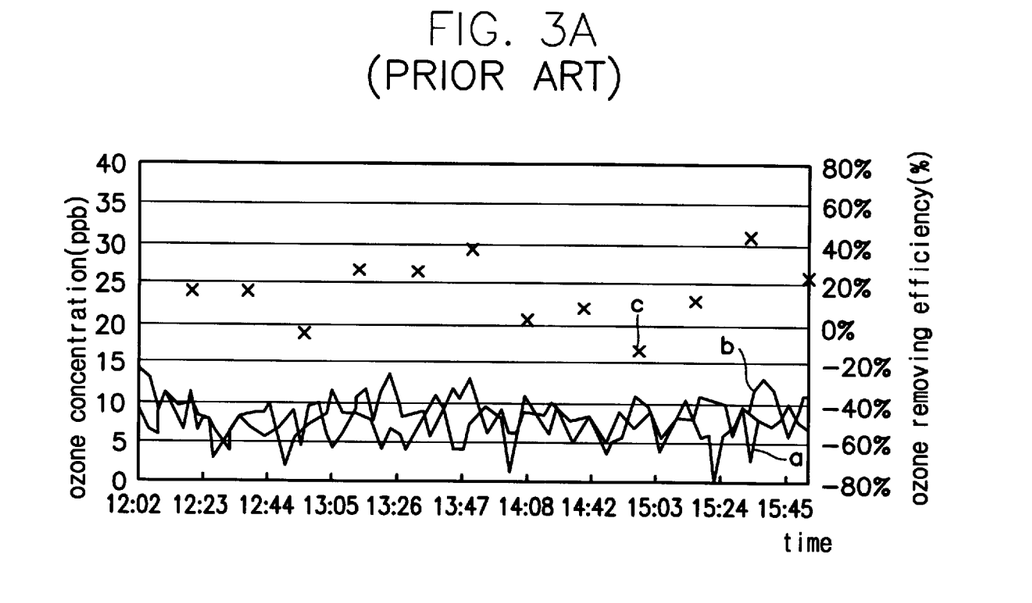
FIGS. 3A and 3B are graphs illustrating ozone-removing efficiencies by utilizing the conventional WSS (FIG. 3A), and the gas purifying system according to a first embodiment of the present invention (FIG. 3B)
Figure 3B:
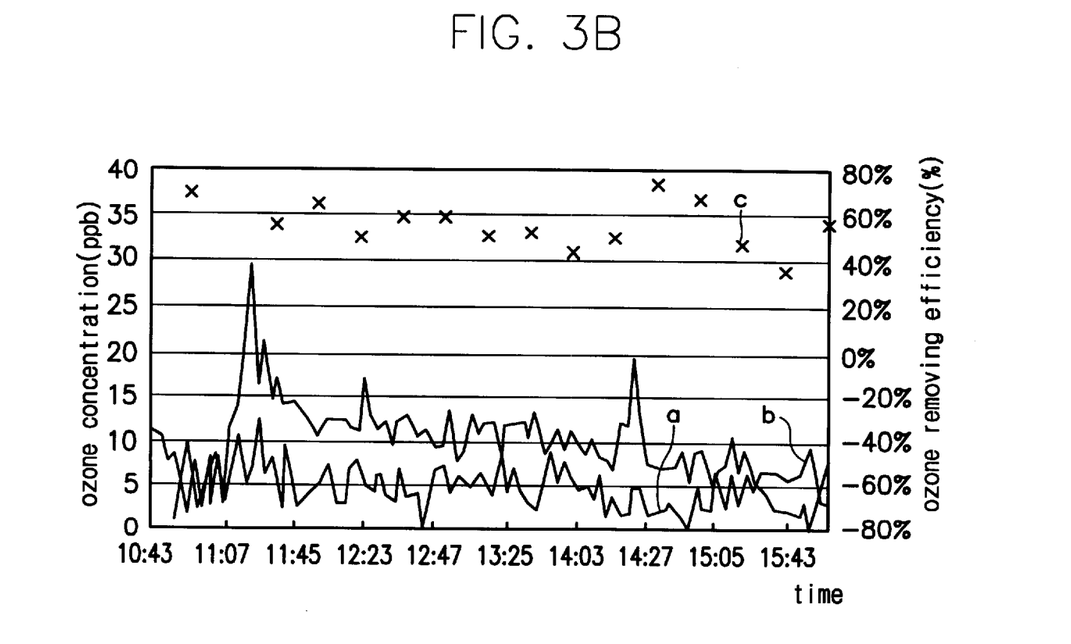

FIGS. 3A and 3B are graphs illustrating ozone-removing efficiencies utilizing a conventional WSS (FIG. 3A), and the gas purifying system according to a first embodiment of the present invention (FIG. 3B). The collecting apparatus is manufactured from $TiO_2$ and has mesh-shaped collecting plates. The distance between the collecting plates was 1 cm and the thickness of the integrated set of collecting plates was 10 cm.

In FIG. 3A, graph 'a' represents the ozone concentration of air (arts per billion—ppb) before passing through the WSS, graph 'b' represents the ozone concentration of air (ppb) after passing through the WSS, and graph 'c' represents the ozone-removing efficiency. For the conventional WSS, the ozone removing efficiency is about −12 to 45% and the mean value is 16.8%. When compared with ambient air, it is confirmed that the conventional WSS has an irregular ozone removing efficiency.

In FIG. 3B, graph 'a' represents the ozone concentration of air (ppb) before passing through the gas purifying system according to the first embodiment of the present invention, graph 'b' represents ozone concentration of air (ppb) after passing though the gas purifying system according to a first embodiment of the present invention, and graph 'c' represents the ozone removing efficiency. The ozone removing efficiency is about 37–75% and the mean value is 56.8%. It can be readily be seen that the ozone removing efficiency is vastly improved by utilizing the gas purifying system according to the present invention when comparing with the conventional WSS.

In the inventive gas purifying system, the particles are first collected by minute water droplets generated from the nozzles, and then collide with the eliminator to be removed. Thereafter, any remaining gaseous contaminating materials can be removed by the collecting apparatus installed at the rear portion of the eliminator. The operating principles of the collecting apparatus will be described in detail below with reference to the second embodiment of the invention.

Figure 4:
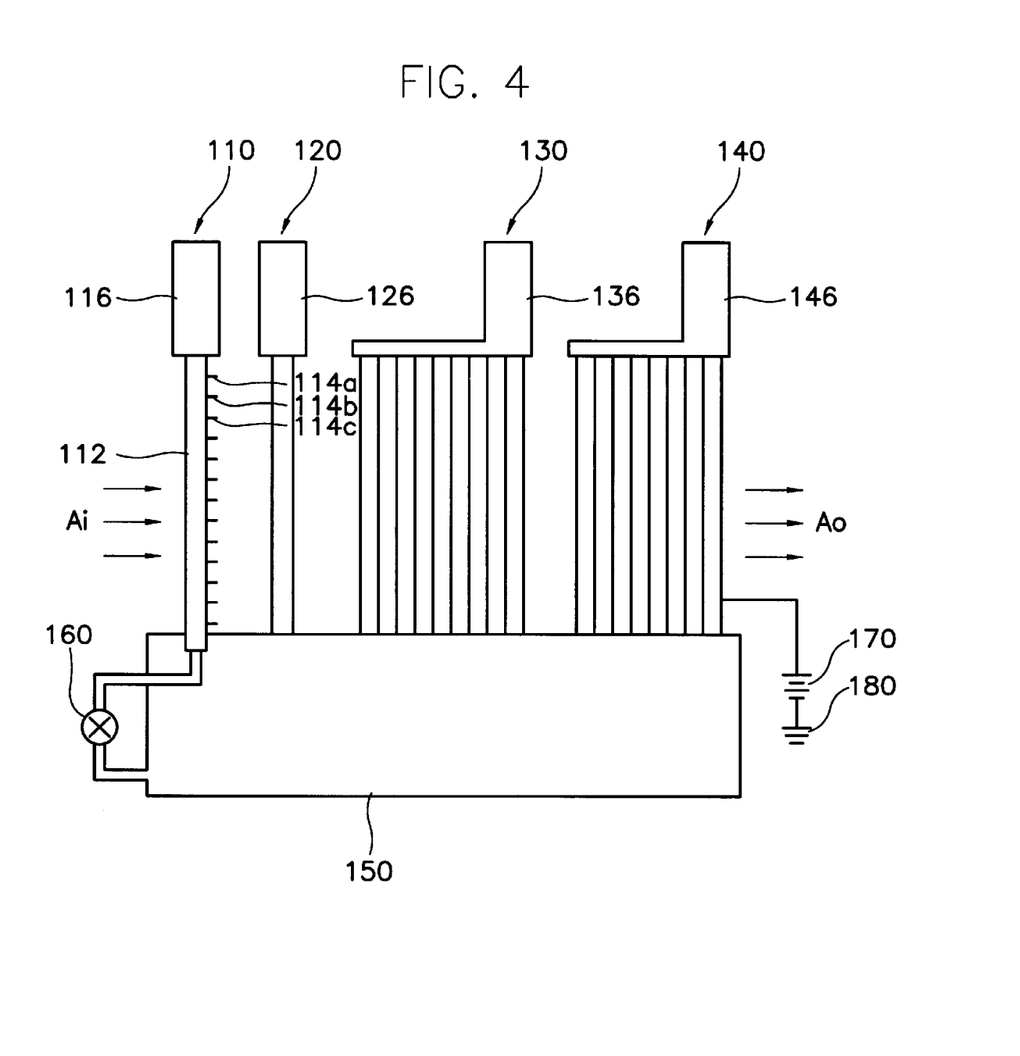
FIG. 4 is a schematic side view of a gas purifying system according to a second embodiment of the present invention.

FIG. 4 is a schematic side view of a gas purifying system according to a second embodiment of the present invention. According to this embodiment, an electrical energy source 170 and a ground device 180 are added to the collecting apparatus 140 for the gas purifying system disclosed in the first embodiment. Preferably, the collecting plates 142a, 142b, 142c, ... 142n forming the collecting apparatus 140 are electrically connected to the source of electrical energy 170. The collecting apparatus supporter 146 is composed of a conductive material so as to apply the electrical energy to one portion of the collecting apparatus supporter.

Upon application of the electrical energy, electrons are emitted from the collecting apparatus 140 and the contaminating materials are collected by the collecting apparatus by means of an interaction of the electrons with the water droplets originating from the WSS in the front portion of the system. When the amount of emitted electrons is increased, the collecting efficiency of the contaminating materials can be improved. In this embodiment, the amount of emitted electrons is increased by applying electrical energy to the collecting apparatus 140. Table 1 illustrates the removing efficiency of the contaminating materials when subjected to various forms of electrical energy, whether alternating current or direct current.

TABLE 1

Removing Efficiency by Application of Electrical Energy

| Condition | | | O-zone | Ozone Exhausting Amount (E.A.) Ozone Removing Efficiency (R.E.) | | | | | |
|---|---|---|---|---|---|---|---|---|---|
| | | | | 0KV | | AC 220V | | DC 380V | |
| Hu-midity (RH) | Temp (° C.) | Stan-dard (ppb) | Amt (ppb) | E.A (ppb) | R.E. (%) | E.A (ppb) | R.E. (%) | E.A (ppb) | R.E. (%) |
| 17 | 19 | 26 | 350 | 171 | 55.0 | 150 | 61.7 | 145 | 63.3 |
| 21 | 18 | 11 | 150 | 40 | 79.1 | 38 | 80.6 | 40 | 79.1 |
| 38 | 22 | 25 | 160 | 70 | 66.7 | 42 | 87.4 | — | — |

As shown in Table 1, as the relative humidity (RH) is increased the ozone removing efficiency (R. E.) is improved. The indicated temperature was room temperature, and it is noted that the ozone removing efficiency is not largely dependent on changes in room temperature. The Standard column refers to the amount of ozone (ppb) contained in the inflowing gas. The experiments were conducted under three different conditions, namely, no applied voltage, an alternating current of 220 V applied, and a direct current of 380 V applied.

Through the experiments, it was confirmed that an improved ozone removing efficiency is obtained when voltage is applied as compared to a case where no voltage is applied. The maximum ozone removing efficiency was 87.4%. Also, note that in those cases where voltage was applied, approximately the same ozone removing efficiency was realized, regardless of whether alternating current or direct current was applied.

The principle behind the removing of the contaminating materials by the collecting apparatus will now be described in greater detail. Materials that emit electrons when subjected to visible light, ultraviolet light and electrical energy, such as ZnO, CdS, $WO_3$, $TiO_2$, etc., function as catalysts. As is well known, a catalyst is a compound, which can change a reaction velocity or initiate a chemical reaction, while the catalyst itself is not changed. The above-described electron emitting materials function as the catalyst when subjected to light or electrical energy. These compounds emit photoelectrons when subjected to light energy near 400 Å, which corresponds to near ultraviolet or visible light. Photoelectrons are electrons emitted from atoms, molecules or solids by ionization due to light or external photoelectron effect. When the wavelength of the light is below the critical wavelength, the photoelectron emitting phenomena occurs. In fact, these kinds of materials can emit photoelectrons when subjected to natural sunlight, whereby the contaminating materials can be removed even though an external energy source is not applied.

In practice, a separate ultraviolet lamp can be installed at the collecting apparatus to radiate ultraviolet light onto the catalyst to improve the emitting effect. However, the installation of the ultraviolet lamp is cumbersome, and it increases the footprint or floor area required for the purifying system. On balance, it is better to install the ultraviolet lamp, as the benefits outweigh the drawbacks.

When a trace amount of ferrous or silicon is added into the electron emitting materials, the electron emitting efficiency is improved and an excellent contaminating removing efficiency can be accomplished even under fluorescent or incandescent lamps. Alternatively, as described above, an electrical voltage may be applied to the electron emitting materials to improve the electron emitting efficiency and a good contaminating removing efficiency can be obtained through this operation.

The exact mechanics of the reaction between the emitted photoelectrons with water and the contaminating materials cannot be precisely verified. However, it is understood that the photoelectron reacts with dissolved oxygen in water or hydrogen peroxide to produce an OH radical. The OH radical also is produced by holes formed at the surface of the electron emitting material. The OH radical has a high oxidizing power which is about 2.07 times that of chlorine ($Cl_2$) and about 1.16 times that of ozone ($O_3$) The high oxidizing power can decompose the organic compounds into carbon dioxide and water, and can treat the heavy metal ions through oxidizing and precipitating functions. Further, since the OH radical can oxidize and destroy the cell membranes of bacteria, mold, etc., a sterilizing and deodorizing effect also can be obtained.

In operation, the inventive gas purifing system first produces minute water droplets by means of the nozzles. The water droplets impact and capture the minute particles, and the thus obtained droplets impact the eliminator to be removed. Any remaining gaseous contaminating materials passing through this first procedure can be charged to anion by electrons generated from the electron emitting materials, and are thereafter removed via attachment to a positive electrode.

The collecting apparatus can be separately installed at an appropriate place to obtain a gas purifiing effect. However, this purifying effect can be improved within a high humidity atmosphere. Therefore, it is preferred that the collecting apparatus be installed at the rear portion (downstream) of the WSS, or downstream of a humidifier for an AHU (air handling unit) which controls the humidity in a clean room.

Figure 5A:
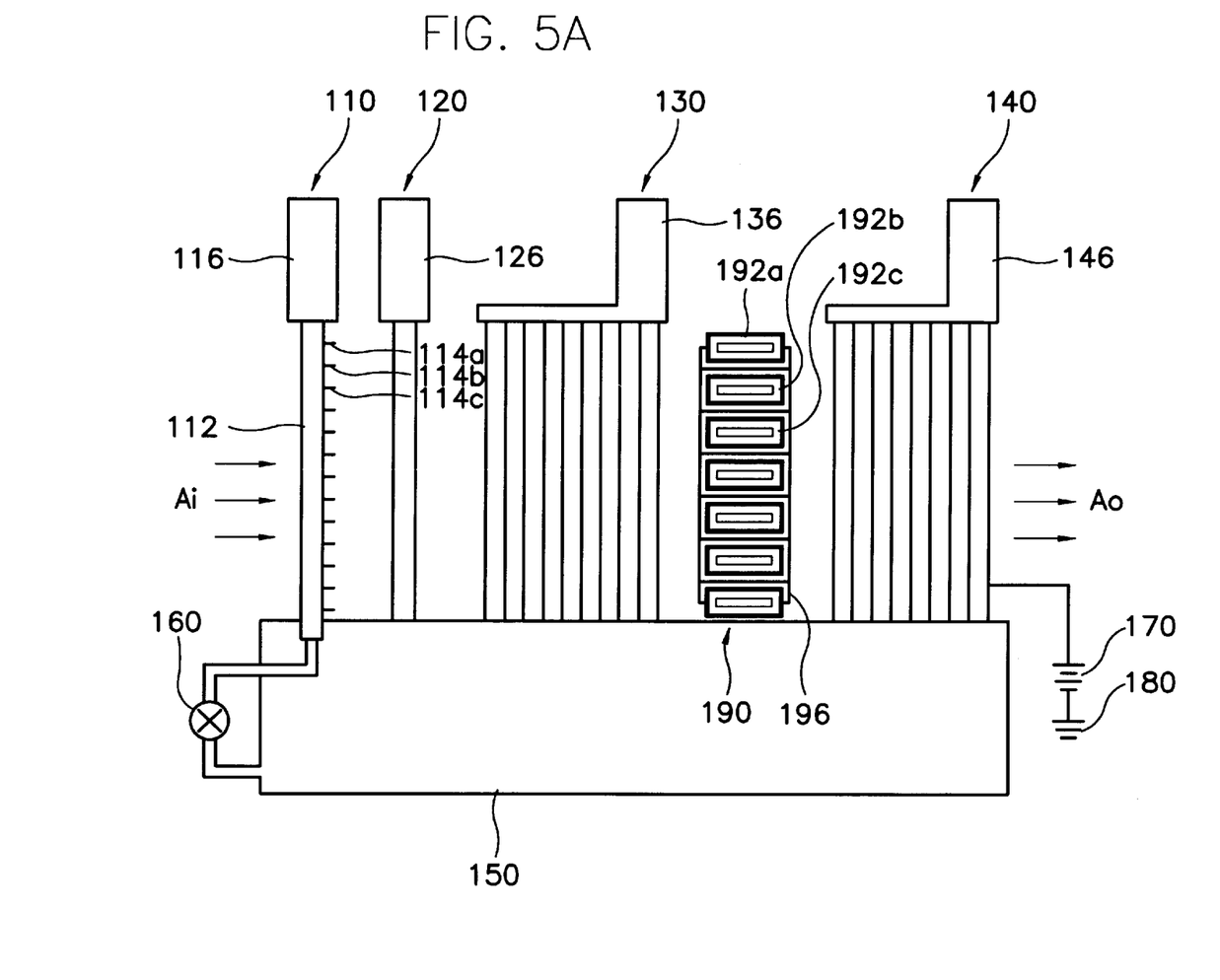
Figure 5B:
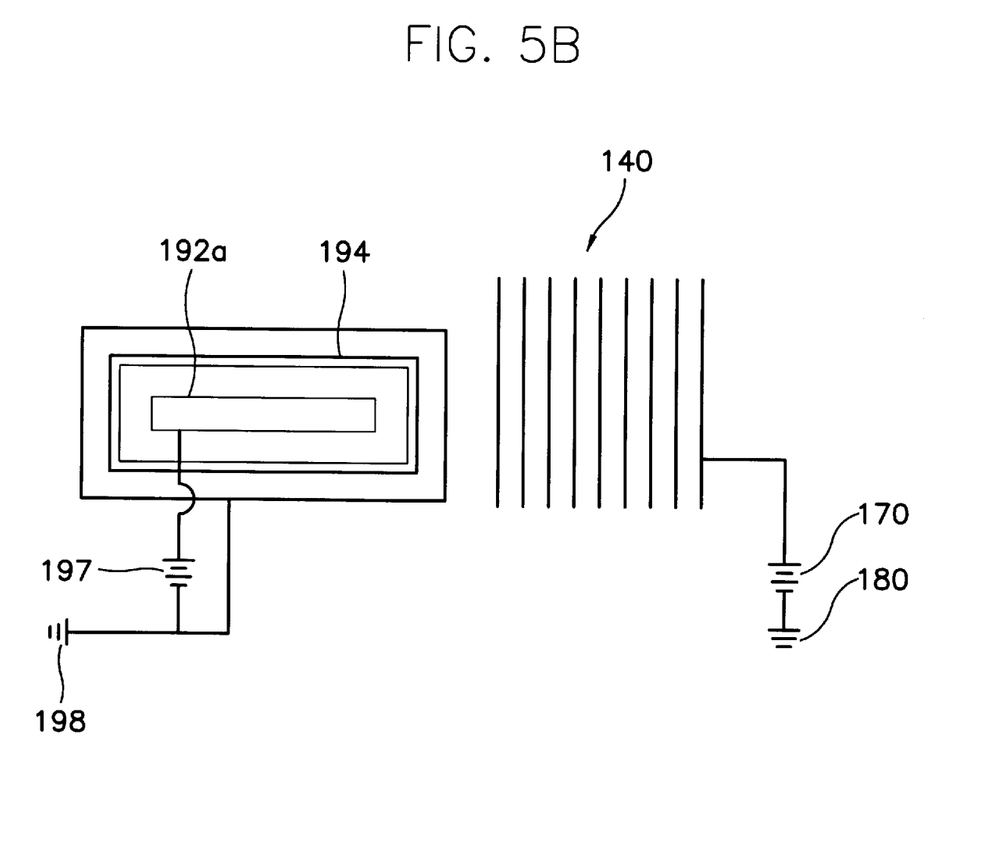

FIGS. 5A and 5B are schematic diagrams of a gas purifying system according to a third embodiment of the present invention, in which FIG. 5A corresponds to a side view and FIG. 5B corresponds to a partial enlarged view of FIG. 5A. In this embodiment, an ultraviolet/photoelectron emitting system 190 is installed between the eliminator 130 and the collecting apparatus 140, which were illustrated in FIGS. 2A and 2B. The ultraviolet/photoelectron emitting system 190 includes at least one ultraviolet lamp, and preferably a plurality of ultraviolet lamps 192a, 192b, 192c, . . . 192n, an ultraviolet electron emitting material 194 surrounding the ultraviolet lamp, which can emit photoelectrons when exposed to ultraviolet light from the ultraviolet lamps, a supporter 196 for supporting the ultraviolet lamps, a voltage applying apparatus 197 for applying voltage to the ultraviolet lamps, and ground device 198. The collecting apparatus 140 is the same as previously described, including power source 170 and ground device 180. At this time, a positive electrical potential is applied to the collecting apparatus 140.

Preferably, for the ultraviolet electron emitting material 194, quartz glass, ITO (indium tin oxide), ZnO, CdS, $WO_3$ or $TiO_2$ are utilized. These materials can be utilized individually or in a mixture, and are generally applied via a coating method.

When ultraviolet light having a higher energy than the photoelectron value is exposed to the photoelectron emitting materials, photoelectrons are emitted as a result of the photoelectron effect. Within a space in which the photoelectrons are emitted, an electrical field is formed with the photoelectron emitting material becoming a low potential. The emitted photoelectrons, or anions formed by air and the photoelectrons, move toward a positive electrode. During the movement, the contaminating materials attach onto the anions to be negatively charged. The negatively charged contaminating materials are transferred to the positive electrode and are then collected by the positive electrode. Through this procedure, the inner closed space can be purified. That is, the contaminating materials can be removed by the three steps of generating the anions from the photoelectrons, negatively charging the contaminating materials, and capturing of the charged contaminating materials by an electrical field.

In this embodiment, there is an increase in the removing efficiency of the contaminating materials. It is preferred that a positive electrical potential is applied to the collecting apparatus so as to advantageously collect the negatively charged particles. In operation, the inventive gas purifying system of this embodiment first produces minute water droplets by means of the nozzles. The water droplets impact and capture the minute particles, and the thus obtained droplets impact the eliminator to be removed. Second, photoelectrons generated from the ultraviolet/photoelectron system move toward a positive electrode. During this movement, the photoelectrons capture remaining gaseous contaminating materials within the nearby space, and thus charged anions are attached to the positive electrode and removed. After implementing these procedures, any remaining gaseous contaminating materials passing through the first two procedures can be charged to anion by electrons generated from the electron emitting materials, and are thereafter removed via attachment to a positive electrode.

Since the gas purifying system of the present invention includes both the WSS for advantageously removing aqueous contaminating materials and various floating dusts, and a collecting apparatus for effectively removing organic and non-aqueous contaminating materials, various contaminating materials can be effectively removed by the purifying system of the present invention.

The conventional filters for removing various contaminating materials can be replaced with the gas purifying system of the present invention. Also, externally exhausting gases passed through filters such as general exhausting gas, thermal exhausting gas, organic exhausting gas, acid exhausting gas, alkali exhausting gas, arsenic exhausting gas, etc. can be recirculated after passing through the gas purifying system of the present invention.

In particular, since the purifying system according to the present invention has a good removing efficiency of organic materials and ozone, this system can be applied in a clean room for manufacturing giga- type semiconductor devices. Further, the size of the system can be advantageously controlled by controlling the integrating area and the number of the collecting plates integrated into the collecting apparatus.

While the present invention was described in detail referring to the attached embodiments, various modifications, alternate constructions and equivalents may be employed without departing from the true spirit and scope of the present invention as set forth in the appended claims.

What is claimed is:

1. A gas purifying system for removing molecular contaminants from the air in a room, said system comprising:
a water spraying apparatus that sprays water droplets into incoming air to be purified; and
a collecting apparatus disposed downstream of said water spraying apparatus in the direction of air flow through the system, said collecting apparatus comprising a plurality of planar collecting plates spaced from one another in the direction of air flow through the system, each of said collecting plates comprising electron emitting material that emits electrons, and each of said collecting plates having a plurality of openings therethrough, and intersection points at which the electron emitting material exists between adjacent ones of the openings, said collecting plates being disposed in an offset positional relationship relative to each other wherein the intersection points of an upstream collecting plate confront the openings in a collecting plate disposed downstream thereof in the direction of air flow through the system.

2. The gas purifying system as claimed in claim 1, wherein said electron emitting material emits electrons when exposed to light.

3. The gas purifying system as claimed in claim 1, wherein said electron emitting material emits electrons when supplied with electrical energy.

4. The gas purifying system as claimed in claim 1, wherein said electron emitting material comprises at least one material selected from the group consisting of ZnO, CdS, $WO_3$, $TiO_2$.

5. The gas purifying system as claimed in claim 4, wherein said electron emitting material further comprises an amount of ferrous or silicon.

6. The gas purifying system as claimed in claim 1, wherein each of said collecting plates is a porous plate.

7. The gas purifying system as claimed in claim 1, wherein each of said collecting plates is a mesh-shaped plate having repeating rows and columns of crossing wires arranged at 90 degree angles relative to one another.

8. The gas purifying system as claimed in claim 1, wherein each of said collecting plates is a honey comb-shaped plate having hexagonal portions.

9. The gas purifying system as claimed in claim 1, wherein said water spraying apparatus is a humidifier.

10. The gas purifying system as claimed in claim 3, wherein the collecting apparatus further comprises an electrical energy source and a ground connected to said collecting plates.

11. The gas purifying system as claimed in claim 1, and further comprising an ultraviolet lamp, and an ultraviolet photoelectron emitting material that emits electrons when exposed to ultraviolet light, said ultraviolet photoelectron emitting material surrounding the ultraviolet lamp, and wherein the ultraviolet lamp and the ultraviolet photoelectron emitting material are disposed between said water spraying apparatus and said collecting apparatus in the direction of air flow through the system.

12. The gas purifying system as claimed in claim 11, wherein said ultraviolet photoelectron emitting material comprises at least one material selected from the group consisting of quartz glass, ITO (indium tin oxide), ZnO, CdS, $WO_3$, $TiO_2$.

13. The gas purifying system as claimed in claim 11, wherein said electron emitting material of the collecting plates emits electrons when supplied with electrical energy, and the collecting apparatus further comprises an electrical energy source and a ground connected to said collecting plates.

* * * * *